(12) United States Patent
Stanton (10) Patent No.: US 11,857,466 B2
(45) Date of Patent: Jan. 2, 2024

(54) TABLE SYSTEM FOR MEDICAL IMAGING

(71) Applicant: Mobius Imaging, LLC, Shirley, MA (US)

(72) Inventor: Russell Stanton, Lunenberg, MA (US)

(73) Assignee: Mobius Imaging, LLC, Shirley, MA (US)

( * ) Notice: Subject to any disclaimer, the term of this patent is extended or adjusted under 35 U.S.C. 154(b) by 249 days.

(21) Appl. No.: 17/190,481

(22) Filed: Mar. 3, 2021

(65) Prior Publication Data

US 2021/0186790 A1 Jun. 24, 2021

Related U.S. Application Data

(63) Continuation of application No. 15/685,955, filed on Aug. 24, 2017, now Pat. No. 10,980,692.

(Continued)

(51) Int. Cl.
*A61G 7/10* (2006.01)
*A61G 13/04* (2006.01)
(Continued)

(52) U.S. Cl.
CPC .............. *A61G 13/04* (2013.01); *A61B 5/704* (2013.01); *A61B 6/0442* (2013.01); *A61B 5/055* (2013.01);
(Continued)

(58) Field of Classification Search
CPC ........ A61B 6/04; A61B 6/0457; A61G 13/04; A61G 7/10; A61G 7/1057; A61G 7/1017; A61G 7/1044
See application file for complete search history.

(56) References Cited

U.S. PATENT DOCUMENTS 3,554,598 A 1/1971 Dunkin
3,866,973 A 2/1975 Heubeck
(Continued)

FOREIGN PATENT DOCUMENTS

CN 1178457 A 4/1998
CN 1392788 A 1/2003
(Continued)

OTHER PUBLICATIONS

English language abstract for CN 1392788 A extracted from espacenet.com database on Jul. 22, 2021, 1 page.
(Continued)

*Primary Examiner* — Justin C Mikowski
*Assistant Examiner* — Ifeolu A Adeboyejo
(74) *Attorney, Agent, or Firm* — Howard & Howard Attorneys PLLC (57) ABSTRACT

A table system for use with an imaging device includes a base portion that supports the table system over a support surface, a patient support including a platform for supporting a patient in a standing position and a bed for supporting the patient in a lying position, a linkage portion coupled between the base portion and the patient support that is pivotable with respect to both the base portion and the patient support, a first drive mechanism that drives the pivoting of the patient support with respect to the linkage portion, and a second drive mechanism that drives the pivoting of the linkage portion with respect to the base portion, the first and second drive mechanisms moving the patient support between a vertical position in which the platform is substantially parallel to the support surface and a horizontal position in which the bed is substantially parallel to the support surface.

20 Claims, 6 Drawing Sheets

Related U.S. Application Data (60) Provisional application No. 62/380,595, filed on Aug. 29, 2016.

(51) Int. Cl.
  *A61B 5/00* (2006.01)
  *A61B 6/04* (2006.01)
  *A61B 5/055* (2006.01)

(52) U.S. Cl.
  CPC .......... *A61B 6/0407* (2013.01); *A61B 6/0487* (2020.08); *A61G 2210/50* (2013.01)

(56) References Cited

U.S. PATENT DOCUMENTS

| | | | |
|---|---|---|---|
| 3,874,728 | A | 4/1975 | Weiland |
| 3,927,326 | A * | 12/1975 | Kunne ................. A61B 6/4452 378/189 |
| 4,926,457 | A * | 5/1990 | Poehner ............... A61G 7/0509 5/81.1 R |
| 4,928,283 | A | 5/1990 | Gordon |
| 5,015,035 | A | 5/1991 | Stoeckl et al. |
| 5,149,074 | A | 9/1992 | Jarin |
| 5,448,607 | A | 9/1995 | McKenna |
| 5,572,569 | A * | 11/1996 | Benoit ..................... A61B 6/04 5/601 |
| 5,574,763 | A * | 11/1996 | Dehner ................... A61B 6/50 378/20 |
| 5,581,166 | A * | 12/1996 | Eismann ................... B25J 9/04 318/568.22 |
| 5,740,222 | A | 4/1998 | Fujita et al. |
| 5,781,705 | A * | 7/1998 | Endo ..................... B25J 9/1643 318/568.22 |
| 5,790,996 | A | 8/1998 | Narfstrom |
| 5,794,286 | A | 8/1998 | Scott et al. |
| 5,810,006 | A | 9/1998 | Votruba et al. |
| 5,883,937 | A | 3/1999 | Schmitt |
| 6,094,760 | A | 8/2000 | Nonaka et al. |
| 6,104,775 | A | 8/2000 | Tuy |
| 6,212,251 | B1 | 4/2001 | Tomura et al. |
| 6,237,172 | B1 * | 5/2001 | Morgan, Sr. ........... A61G 13/12 5/617 |
| 6,298,854 | B1 | 10/2001 | Sundstrom |
| 6,426,989 | B2 | 7/2002 | Grass et al. |
| 6,490,333 | B1 | 12/2002 | Hsieh |
| 6,640,363 | B1 | 11/2003 | Pattee et al. |
| 6,988,827 | B1 | 1/2006 | Mueller |
| 6,996,204 | B2 | 2/2006 | Grass et al. |
| 7,001,045 | B2 | 2/2006 | Gregerson et al. |
| 7,077,569 | B1 | 7/2006 | Tybinkowski et al. |
| 7,175,347 | B2 | 2/2007 | Tybinkowski et al. |
| 7,215,805 | B2 | 5/2007 | Bruder et al. |
| 7,224,764 | B2 | 5/2007 | Sukovic et al. |
| 7,302,038 | B2 | 11/2007 | Mackie et al. |
| 7,388,941 | B2 | 6/2008 | Sukovic et al. |
| 7,394,888 | B2 | 7/2008 | Sukovic et al. |
| 7,397,895 | B2 | 7/2008 | Bailey et al. |
| 7,568,836 | B2 | 8/2009 | Bailey et al. |
| 7,637,660 | B2 | 12/2009 | Tybinkowski et al. |
| 7,640,607 | B2 * | 1/2010 | Guertin ................. A61B 6/4441 5/601 |
| 7,963,696 | B2 | 6/2011 | Bailey et al. |
| 8,118,488 | B2 | 2/2012 | Gregerson |
| 8,251,584 | B2 | 8/2012 | Tybinkowski et al. |
| 8,482,242 | B2 * | 7/2013 | Nakasugi ............... B25J 9/1633 318/568.22 |
| 8,674,326 | B2 | 3/2014 | Iwata |
| 8,705,695 | B2 | 4/2014 | Jabri et al. |
| 8,737,708 | B2 | 5/2014 | Hartmann et al. |
| 8,740,880 | B2 * | 6/2014 | Pinault ................... A61N 5/1049 606/1 |
| 8,746,973 | B2 | 6/2014 | Gregerson et al. |
| 8,819,877 | B2 | 9/2014 | Zheng et al. |
| 8,888,364 | B2 | 11/2014 | Bailey et al. |
| 9,016,941 | B2 | 4/2015 | Tybinkowski et al. |
| 9,301,726 | B2 * | 4/2016 | Mackie ................. A61B 6/032 |
| 9,398,886 | B2 | 7/2016 | Gregerson et al. |
| 9,662,256 | B2 | 5/2017 | Marle et al. |
| 9,795,022 | B2 | 10/2017 | Duhamel |
| 9,820,704 | B2 | 11/2017 | Tybinkowski et al. |
| 10,178,981 | B2 | 1/2019 | Bailey et al. |
| 2005/0135560 | A1 | 6/2005 | Dafni et al. |
| 2006/0002511 | A1 | 1/2006 | Miller et al. |
| 2010/0275927 | A1 * | 11/2010 | Saracen ................ A61B 6/0487 128/845 |
| 2011/0222667 | A1 | 9/2011 | Gregerson et al. |
| 2011/0224475 | A1 * | 9/2011 | Schreuder ............ A61G 13/101 128/845 |
| 2014/0003572 | A1 | 1/2014 | Gregerson et al. |
| 2014/0067118 | A1 * | 3/2014 | Gomi ..................... B25J 9/1651 901/9 |
| 2014/0139215 | A1 | 5/2014 | Gregerson et al. |
| 2014/0265182 | A1 | 9/2014 | Stanton et al. |
| 2014/0275953 | A1 | 9/2014 | Gregerson et al. |
| 2015/0208992 | A1 * | 7/2015 | Marash .................. A61B 6/032 600/407 |
| 2015/0313557 | A1 | 11/2015 | Mackie et al. |
| 2016/0302871 | A1 | 10/2016 | Gregerson et al. |
| 2017/0007334 | A1 | 1/2017 | Crawford et al. |
| 2017/0215825 | A1 | 8/2017 | Johnson et al. |
| 2017/0215826 | A1 | 8/2017 | Johnson et al. |
| 2017/0215827 | A1 | 8/2017 | Johnson et al. |
| 2018/0055707 | A1 | 3/2018 | Stanton |
| 2018/0177473 | A1 | 6/2018 | Gregerson et al. |
| 2018/0214098 | A1 | 8/2018 | Tybinkowski et al. |

FOREIGN PATENT DOCUMENTS

| | | |
|---|---|---|
| CN | 102188778 A | 9/2011 |
| CN | 103549970 A | 2/2014 |
| CN | 204618273 U | 9/2015 |
| DE | 102015110196 A1 | 12/2015 |
| EP | 1129664 B1 | 7/2006 |
| EP | 1787614 A2 | 5/2007 |
| EP | 1810652 A2 | 7/2007 |
| GB | 893770 A | 4/1962 |
| JP | 2000214263 A | 8/2000 |
| JP | 2006255090 A | 9/2006 |

OTHER PUBLICATIONS

English language abstract and machine-assisted English translation for CN 204618273 U extracted from espacenet.com database on Jul. 22, 2021, 6 pages.

English language abstract for CN 1178457 A extracted from espacenet.com database on Mar. 21, 2022, 2 pages.

English language abstract for CN 102188778 A extracted from espacenet.com database on Mar. 21, 2022, 2 pages.

English language abstract and machine-assisted English translation for CN 103549970 A extracted from espacenet.com database on Mar. 21, 2022, 14 pages.

International Preliminary Report on Patentability (Chapter 1 of the Patent Cooperation Treaty) from the Korean Intellectual Property Office in International Application No. PCT/US2017/048864 dated Mar. 14, 2019.

International Search Report and Written Opinion from the Korean Intellectual Property Office in International Application No. PCT/US2017/048864 dated Dec. 6, 2017.

Machine-Assisted English language abstract and machine-assisted English language translation for DE 10 2015 110 196 extracted from espacenet.com database on Mar. 11, 2020, 15 pages.

* cited by examiner

TABLE SYSTEM FOR MEDICAL IMAGING

CROSS-REFERENCE TO RELATED APPLICATIONS

The subject patent application is a Continuation of U.S. patent application Ser. No. 15/685,955, filed on Aug. 24, 2017, which claims priority to all the benefits of U.S. Provisional Patent Application No. 62/380,595, filed on Aug. 29, 2016, the disclosures of each of which are hereby incorporated by reference in their entirety.

BACKGROUND

A variety of patient supports (e.g., tables) are used for different medical imaging applications, such as x-ray fluoroscopic and computed tomography (CT) imaging and magnetic resonance (MR) imaging. These patient supports are often designed for use with a particular device or type of imaging device. For example, a patient support for an x-ray CT imaging device may be designed and dimensioned for sliding a patient in and out of an imaging bore of the device.

In many cases, it can be difficult to load and unload patients from the supports commonly used with medical imaging equipment. In addition, conventional patient supports may be limited in the types imaging devices they can be used with and/or the positions in which they can support a patient. Conventional patient supports may also need to be made relatively large and/or heavy to minimize dynamic sagging as the support slides in and out of the bore of an imaging device.

There is a continuing need for an improved patient support for medical imaging.

SUMMARY

Embodiments include table systems for use with an imaging device that include a base portion that supports the table system over a support surface, a patient support including a platform sized and shaped to support a patient in a standing position and a bed sized and shaped to support the patient in a lying position, a linkage portion coupled between the base portion and the patient support that is pivotable with respect to both the base portion and the patient support, a first drive mechanism that drives the pivoting of the patient support with respect to the linkage portion, and a second drive mechanism that drives the pivoting of the linkage portion with respect to the base portion, the first and second drive mechanisms moving the patient support between a vertical position in which the platform is substantially parallel to the support surface and a horizontal position in which the bed is substantially parallel to the support surface.

BRIEF DESCRIPTION OF THE DRAWINGS

Other features and advantages of the present invention will be apparent from the following detailed description of the invention, taken in conjunction with the accompanying drawings of which.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

Figure 1:
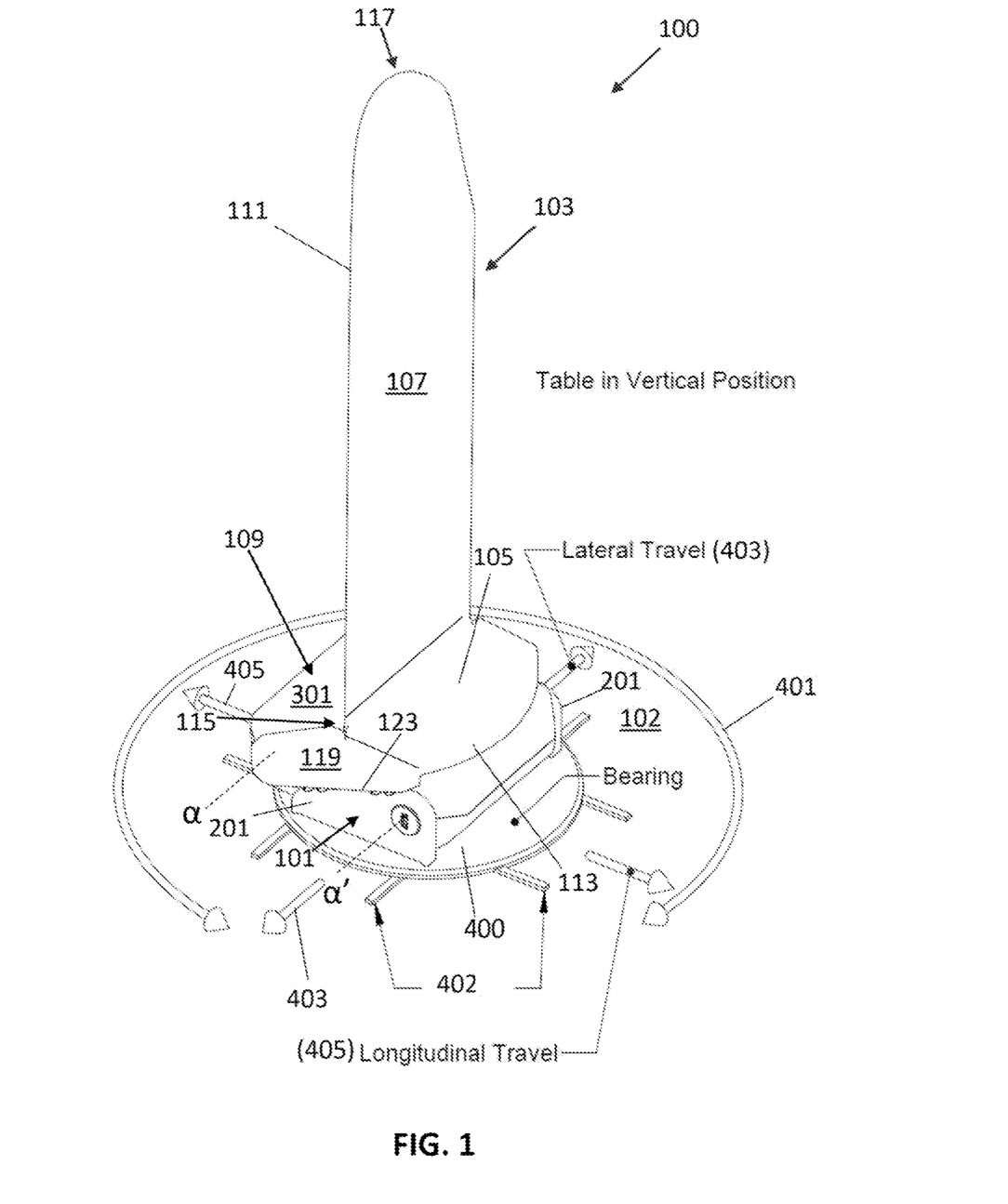
FIG. 1 is a perspective view of a table system with a patient support in a vertical position according to an embodiment.
Figure 2:
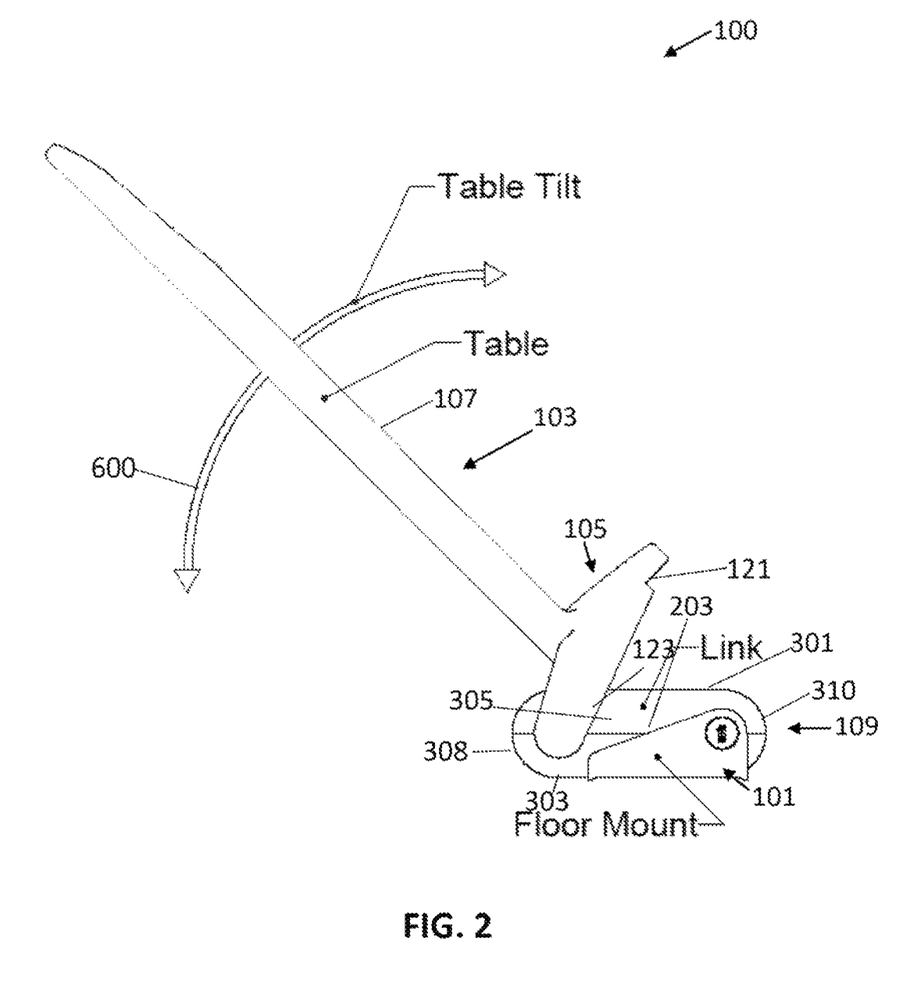
FIG. 2 is a side view of a table system illustrating the pivoting motion of the patient support according to an embodiment.
Figure 3:
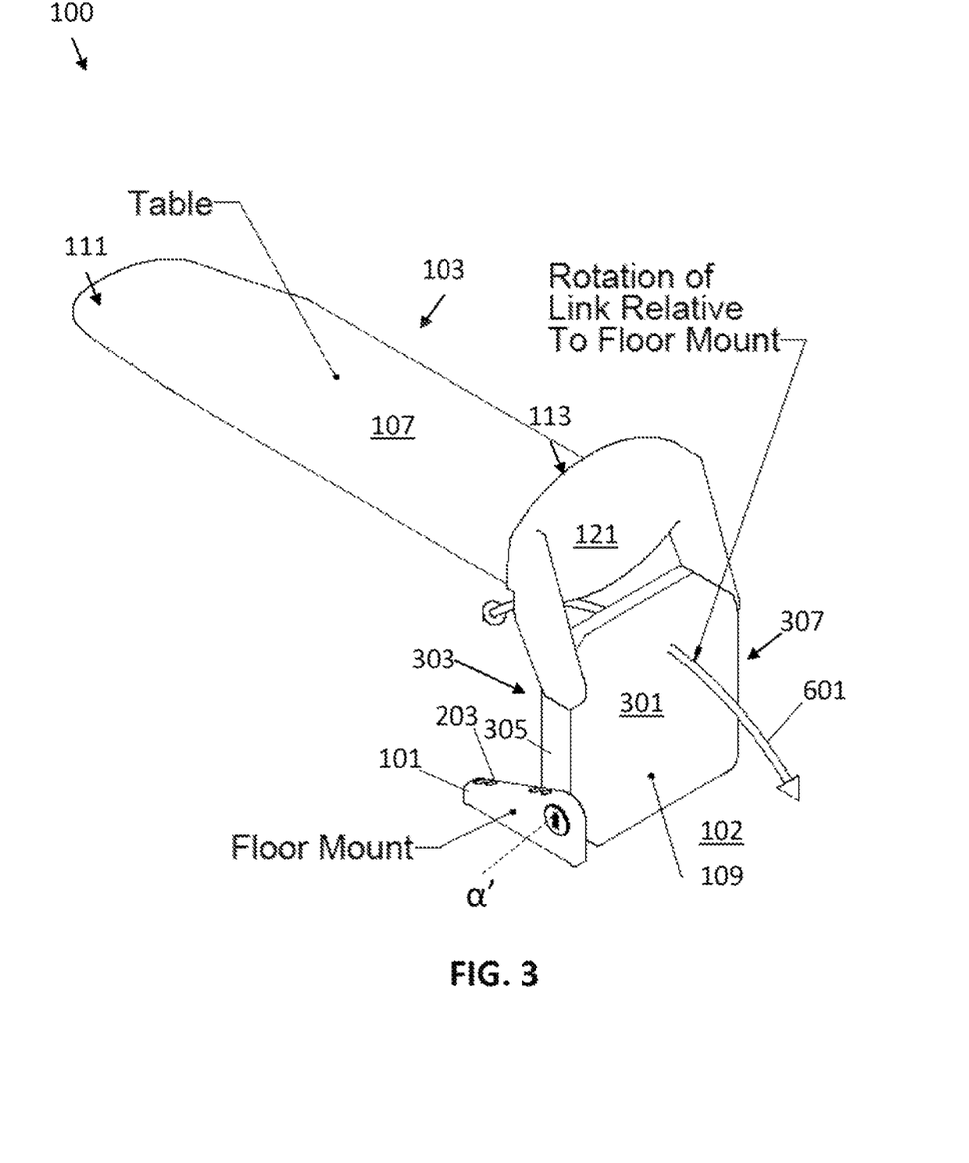
FIG. 3 is a perspective view of a table system with a linkage portion pivoted upwards and the patient support pivoted to a horizontal position.
Figure 4:
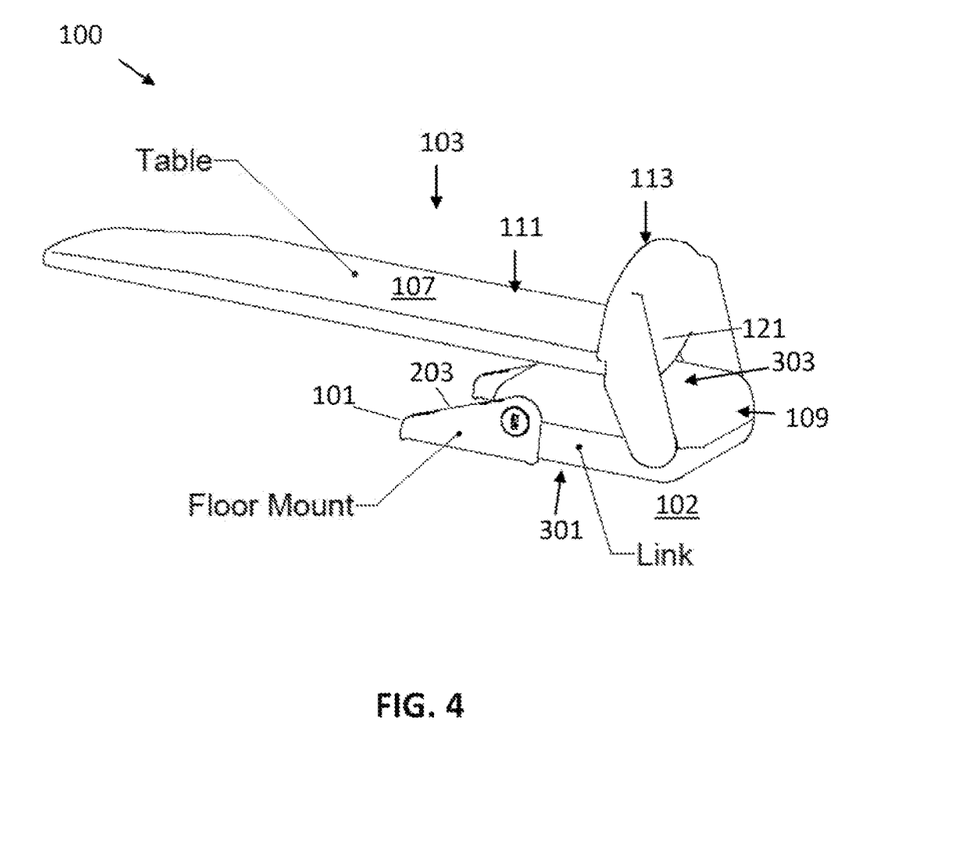
FIG. 4 is a perspective view of a table system with the patient support in a lowered position.
Figure 5:
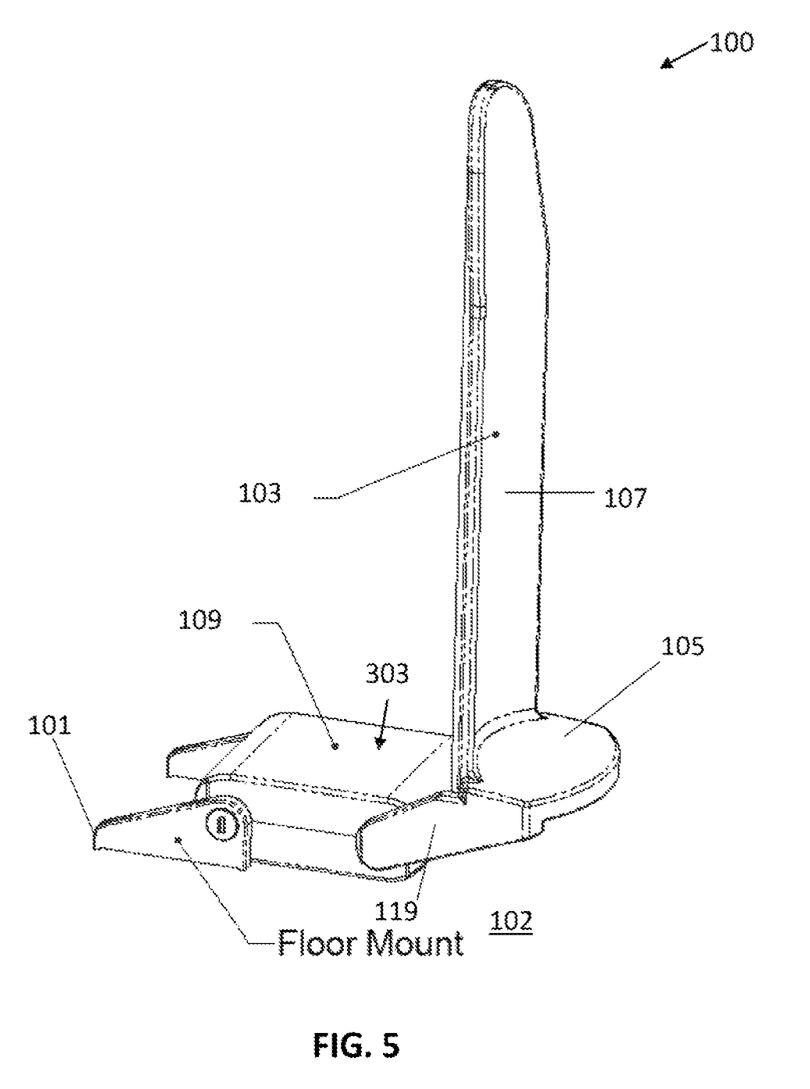
FIG. 5 is a front perspective view of a table system with the patient support pivoted upwards to a vertical position.
Figure 6:
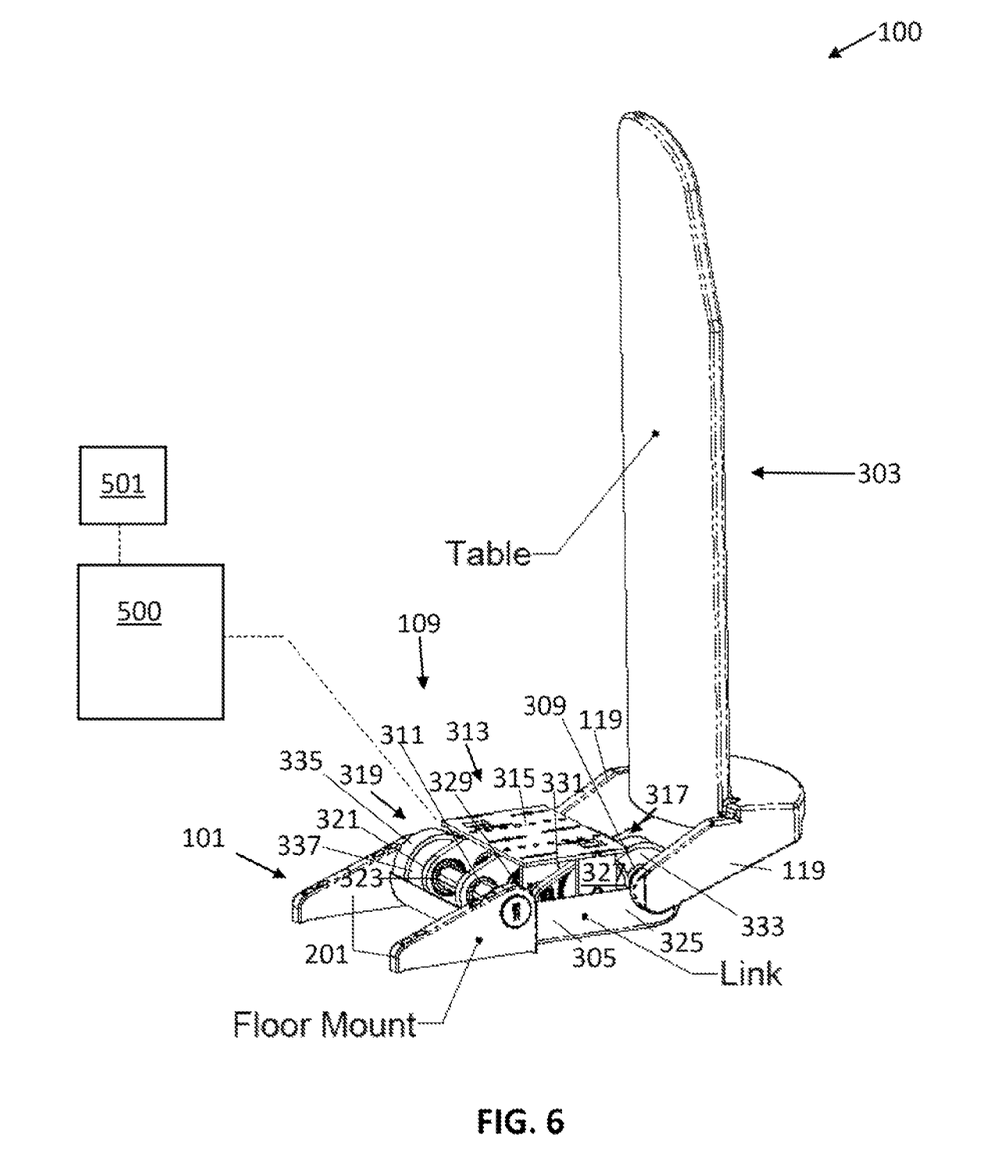
FIG. 6 is a rear perspective view of a table system with a covering of the linkage portion partially removed.

Embodiments include a table system for use with an imaging device, such as a diagnostic medical imaging device. As shown in FIGS. 1-6, a table system 100 according to various embodiments may include a base portion 101 configured to support the table system 100 over a support surface (e.g., a floor 102), a patient support 103 which includes a platform 105 sized and shaped to support a patient in a standing position and a bed 107 sized and shaped to support the patient in a lying position, and a linkage portion 109 coupled between the base portion 101 and the patient support 103 that is pivotable with respect to both the base portion 101 and the patient support 103. A first drive mechanism may be located in the linkage portion 109 and may drive the pivoting of the linkage portion 109 with respect to the patient support 103. A second drive mechanism may also be located in the linkage portion 109 and may drive the pivoting of the linkage portion 109 with respect to the base portion 101. In embodiments, the patient support 103 may be positioned in a vertical position (as shown in FIGS. 1, 5 and 6) in which the platform 105 is substantially parallel to the support surface (e.g., floor 102) and a horizontal position (as shown in FIGS. 3 and 4) in which the bed 107 is substantially parallel to the support surface (e.g., floor 102). As used herein, the term "substantially parallel" means±15° from an exactly parallel position. The patient support 103 may be positioned at any arbitrary angle between a horizontal and vertical configuration. As shown in FIG. 2, for example, the patient support 103 may be tilted at a 45° angle between a vertical and horizontal position. In embodiments, the patient support 103 may stably support the full weight of a human body and may support greater than 200 kg, such as up to about 800 kg, over the full range of pivoting motions of the patient support 103 and linkage portion 109.

The patient support 103 may include an elongated first portion 111 having a surface forming the bed 107 which may support a patient in a lying or inclined position and a second portion 113 having a surface forming the platform 105 which may support a patient in a weight-bearing standing or inclined position. The first portion 111 may have a length dimension that is preferably greater than the average height of an adult human, such as between 2-3 meters (e.g., about 2.5 meters). The second portion 113 may extend substantially perpendicular to the first portion 111 at a first end 115 of the first portion 111. As used herein, the term "substantially perpendicular" means±15° from an exactly perpendicular position. The second portion 113 may have a length dimension that is less than the length dimension of the first portion 111. In embodiments, the length dimension of the second portion 113 may be between 20-50 cm (e.g., about 35 cm), and may be greater than the average foot length of an adult human to enable a patient to comfortably stand on the platform 105. The width of the first and second portions 111, 113 may be greater than the average width of an adult human (e.g., average shoulder width in the case of the first portion 111 and/or average stance width in the case of the second portion 113) and may be at least about 40 cm. The width of the first and/or second portions 111, 113 may be less than a bore diameter of a medical imaging device (e.g., an x-ray CT scanner or MRI device), such as less than about 120 cm, and may be between about 50 and 80 cm.

The bed 107 of the first portion 111 may be concavely curved, as is most clearly visible in FIG. 5. The distal end 117 of the first portion 111 may have a curved edge, as shown for example, in FIG. 1. The platform 105 of the second portion 113 may also have a similar curved edge. The rounded and/or curved surfaces of the patient support 103 may help to minimize beam attenuation by the patient support 103 during an imaging scan.

As shown in FIGS. 1-6, the patient support 103 may include a pair of bracket members 119 that may extend away from a rear surface 121 of the second portion 113 of the patient support 103 (i.e., opposite the platform 105, as shown in FIGS. 2-4). The bracket members 119 may be connected to the linkage portion 109 along an axis a to enable the patient support 103 to pivot with respect to the linkage portion 109, as described in further detail below.

The patient support 103 may be made of one or more suitable high-strength materials. In preferred embodiments, the patient support 103 may be made of a radiolucent (i.e., x-ray transparent) material, such as carbon fiber. In one embodiment, the patient support 103 may comprise a single piece of carbon fiber that may form at least the bed 107 and the platform 105. The carbon fiber element may form a rigid outer shell that may contain a suitable lightweight and radiolucent filler material, such as a foam. The patient support 103 may include additional structural reinforcing elements (e.g., plates, rods, brackets, etc.) that may or may not be radiolucent. For example, the patient support 103 may include one or more metal (e.g., aluminum, steel, etc.) support plates which may be secured to a carbon fiber patient support structure using fasteners. In embodiments in which the patient support 103 includes structural reinforcing elements made from a non-radiolucent material, such as aluminum, the non-radiolucent material may preferably be located so as not to interfere with an imaging scan of a patient on the patient support 103. For example, in the embodiment of FIGS. 1-6, an aluminum support frame may be confined to the brackets 119, at or near to the rear surface 121 of the second portion 113 and/or adjacent to the first end 115 of the first portion 111. This may enable a patient standing on the platform 105 to be scanned over the entire length of the body including through the feet without interference (i.e., image artifacts) from non-radiolucent reinforcing element(s).

The base portion 101 of the table system 100 may include a pair of parallel bracket members 201. The bracket members 201 may be fixed to the floor or other stable support surface using fasteners, such as bolts. The bracket members 201 of the base portion 101 may be made of a suitable high-strength structural material, such as aluminum or steel. The bracket members 201 may have an angled upper surface 203 as shown in FIGS. 2-6. The angled upper surface 203 of the bracket members 201 may be complementary to an angled surface 123 of the bracket members 119 of the patient support 103, as shown in FIG. 1. The bracket members 201 of the base portion 101 may be connected to the linkage portion 109 along an axis a' to enable the linkage portion 109 to pivot with respect to the base portion 101 as described in further detail below.

The linkage portion 109 may include a flat first major surface 301 and a flat second major surface 303 that extends parallel to the first surface 301. The bracket members 201 of the base portion 101 and the bracket members 119 of the patient support 103 may connect to the linkage portion 109 via opposing first and second side walls 305, 307 of the linkage portion 109.

A first rotary drive shaft 309 (see FIG. 6) may extend through one or both side walls 305, 307 of the linkage portion 109 and connect to at least one bracket member 119 of the patient support 103. At least one rotary bearing within the linkage portion 109 may enable the first rotary drive shaft to rotate with respect to the linkage portion 109 to pivot the patient support 103 with respect to the linkage portion 109 about axis a.

A second rotary drive shaft 311 (see FIG. 6) may extend through one or both side walls 305, 307 of the linkage portion 109 and connect to at least one bracket member 201 of the base portion 101. At least one rotary bearing within the linkage portion 109 may enable the linkage portion 109 to rotate with respect to the second rotary drive shaft 311 to cause the linkage portion 109 to pivot with respect to the base portion 101 about axis a'.

The linkage portion 109 may be made from durable, high-strength material(s) to provide a high degree of structural integrity and to prevent the components within the linkage portion 109 from being damaged. In one embodiment, as shown in FIG. 6, the linkage portion 109 may include a rigid support frame 313 made from a suitable high-strength metal material, such as aluminum or steel. The support frame 313 may include a support plate 315 extending adjacent and parallel to the first major surface 301 of the linkage portion 109. A similar support plate may extend adjacent and parallel to the second major surface 303 of the linkage portion 109. First and second drive systems 317, 319 for driving the rotation of the linkage portion 109 with respect to the patient support 103 and base portion 101 may be located at least partially between the two support plates 315. As shown in FIG. 6, one or more block members 321 for supporting rotary bearing(s) 323 for a rotary drive shaft 311 may be secured between the support plates 315. A similar configuration may also be located on the opposite side of the linkage portion 109 to support the other rotary drive shaft 309.

The linkage portion 109 may include an outer shell 325 enclosing an interior housing 327 that may contain the support frame 313, rotary bearings 313, rotary drive shafts 309, 311 and drive systems 317, 319. FIG. 6 illustrates the linkage portion 109 with the outer shell 325 partially removed. The outer shell 325 may define the first and second major surfaces 301, 303 and sidewalls 305, 307, 308 and 310 of the linkage portion 109. As shown, for example, in FIG. 2, the third and fourth sidewalls 308 and 310 of the linkage portion 109 may have a rounded contour to enable the linkage portion 109 to pivot with respect to the ground and the patient support 103 with minimal clearance. In embodiments, the outer shell 325 may be made from a plastic or carbon fiber material.

FIG. 6 illustrates the drive systems 317, 319 for driving the rotation of the rotary drive shafts 309, 311 relative to the linkage portion 109. In embodiments, the drive systems 317, 319 may have a mirrored configuration where two drive systems are rotated 180° within the interior housing 327 of the linkage portion 109. For example, a first drive system 317 for driving the rotation of the first rotary drive shaft 309 may include a first motor 329 between the support plates 315 that may be geared in to a first drive chain 331 that meshes with a first sprocket wheel 333 coupled to the first rotary drive shaft 309. Thus, the first motor 329 may drive the rotation of the first rotary drive shaft 309 and the pivoting of the patient support 103 with respect to the linkage portion 109. A second drive system 319 coupled to the second rotary drive shaft 311 may include a second motor between the support plates 315 (not visible in FIG. 6) that may be geared in to a second drive chain 335 that meshes with a second sprocket wheel 337 coupled to the second rotary drive shaft 311. The second sprocket wheel 337 and the second rotary drive shaft 311 may be fixed to the base portion 101 of the table system 100 (e.g., between bracket members 201). The second motor may drive the second drive chain 335 around the second sprocket wheel 337, causing the linkage portion 109 to rotate on the rotary bearing(s) and pivot with respect to the base portion 101. Rotary encoders may be provided on one or more of the motor, gears or rotary bearings of each of the drive systems 317, 319 for indicating the relative rotational positions of the base portion 101, linkage portion 109 and patient support 103.

As shown in FIG. 1, in some embodiments, the entire table system 100 may be rotated and/or translated along at least one direction. For example, the base portion 101 of the system 100 may be mounted to a platform 400 on a rotating bearing to enable the table system 100 to be rotated in the direction of arrow 401. The rotating platform 400 may be mounted to a rail system 402 to enable the table system 100 to translate in at least one direction, such as along the direction of arrows 403 and/or arrows 405. The rotation and translation motion of the table system 100 may enable a patient to be loaded onto the patient support 103 when the table system 100 in a first position and orientation and then moved to a second position and/or orientation to perform an imaging scan. For example, the table system 100 may be rotated such that the patient support 103 is oriented in line with a patient imaging axis of an imaging device (such as an x-ray CT scanner). Where the imaging device has a fixed bore, the entire table system 100 with the patient supported thereon may be translated into the bore. It is noted that the relative rotational positions of the base portion 101, linkage portion 109 and patient support 103 may remain fixed during the scan such that the torque forces experienced along the length of the patient support 103 remains constant, even when the table system 100 translates into the imaging bore. Thus, there may be no dynamic sagging of the patient support 103 during an imaging scan.

It will be understood that in some embodiments, the table system 100 may be fixed to a floor or other support surface 102 and may not rotate and/or translate as illustrated in FIG. 1.

A control system 500 (e.g., a processor and memory) may be operatively coupled to the table system 100, as schematically illustrated in FIG. 6. The control system 500 may be located partially or completely within the table system 100 (e.g., within the linkage portion 109) and/or within one or more separate components, such as a workstation, an imaging system or a mobile cart. The control system 500 may receive position feedback data (e.g., rotary encoder data) from the table system 100 and may send control signals to the motor(s) of the table system 100 to cause the motors to drive one or both of the rotary drive shafts 309, 311 and pivot the linkage portion 109 and/or the patient support 103 into a desired configuration. The linkage portion 109 and/or the patient support 103 may be pivoted to one or more pre-set configurations of the table system 100 (e.g., stored in the memory of the control system 500) and/or the configuration may be controllably adjusted by a user using a suitable user input device 501 (e.g., buttons, joystick, computer keyboard and/or mouse, touchscreen display, etc.).

Various pivot motions and operating modes of a table system 100 according to an embodiment are now described with reference to FIGS. 1-5. In embodiments, the table system 100 may be used to support a patient while performing a variety of imaging scans of the patient using an imaging system. The imaging system may be an x-ray computed tomography (CT) imaging system. Examples of x-ray CT imaging devices that may be used according to various embodiments are described in, for example, U.S. Pat. No. 8,118,488, U.S. Patent Application Publication No. 2014/0139215, U.S. Patent Application Publication No. 2014/0003572, U.S. Patent Application Publication No. 2014/0265182, U.S. Patent Application Publication No. 2014/0275953, U.S. Provisional Patent Application No. 62/425,746 and U.S. application Ser. No. 15/130,258, the entire contents of all of which are incorporated herein by reference. It will be understood that these embodiments are provided as illustrative, non-limiting examples of imaging systems suitable for use with a table system 100 according to various embodiments, and that an embodiment table system 100 may utilize various types of medical imaging devices. For example, alternatively or in addition to an x-ray CT device, a table system 100 of the various embodiments may be used with an x-ray fluoroscopic imaging device, a magnetic resonance (MR) imaging device, a positron emission tomography (PET) imaging device, a single-photon emission computed tomography (SPECT), an ultrasound imaging device, etc.

In one non-limiting embodiment, the table system 100 may be used to obtain diagnostic images of a patient in a standing or weight-bearing position. A patient may stand on the platform 105 of the patient support 103, optionally with their body leaning or resting against the bed 107. A gantry of an imaging system may be moved such that the patient and patient support 103 are positioned within the bore of the gantry, such as by lowering the gantry over the patient and patient support 103 (or alternatively, raising the patient and patient support 103 into the bore of the gantry). An example of a system for performing an x-ray CT imaging scan of a patient in a weight-bearing position is described in U.S. Patent Application Publication No. 2014/0139215, which was previously incorporated by reference.

In some embodiments, the table system 100 may be used to move a patient between a lying position (i.e., where the patient support 103 extends in a generally horizontal direction with the patient supported primarily by bed 107) and a standing or weight-bearing position (i.e., where the patient support 103 extends in a generally vertical direction with the patient supported primarily by platform 105). In embodiments, a patient may be first loaded onto the patient support 103 in a lying position. The feet of the patient may be adjacent to the platform 105. An optional restraint (e.g., one or more Velcro® straps) may be utilized to secure the patient to the patient support 103. The patient support 103 along with the patient may then be tilted up into a standing or weight-bearing position. Alternately, the patient may be loaded onto the patient support 103 in a standing position (e.g., the patient may step up onto the platform 105) and the patient support 103 along with the patient may be tilted down into a lying position.

FIG. 1 illustrates the table system 100 in a first configuration. In this configuration, the linkage portion 109 lies flat and parallel to the support surface 102 (e.g., the floor). The bracket members 201 of the base portion 101 and the bracket members 119 of the patient support 103 are adjacent to the first and second side walls 305, 307 (see FIGS. 2-3) of the linkage portion 109. The second portion 113 of the patient support 103 may extend over and parallel to the first major surface 301 of the linkage portion 109. The first portion 111 of the patient support 103 may extend vertically upward from and perpendicular to the first major surface 301 of the linkage portion 109. The configuration of FIG. 1 may provide a relatively small footprint with the base portion 101, linkage portion 109 and patient support 103 folded over one another in a compact manner.

FIG. 2 illustrates the pivoting motion of the patient support 103 with respect to the linkage portion 109 in the direction of arrow 600. In FIG. 2, the patient support 103 is tilted about 45° with respect to the linkage portion 109. In embodiments, the patient support 103 may pivot with respect to the linkage portion 109 over a range of at least about 90°, and preferably at least 180° such as up to about 270°.

FIG. 3 illustrates the pivoting motion of the linkage portion 109 with respect to the base portion 101 in the direction of arrow 601. As shown in FIG. 3, the linkage portion 109 is pivoted about axis a' by 90° such that the first and second major surfaces 301, 303 of the linkage portion 109 extend in a vertical direction and are oriented perpendicular to the support surface 102 (e.g., floor). In the configuration of FIG. 3, the patient support 103 is pivoted 180° relative to the configuration of FIG. 1, such that the second portion 113 of the patient support 103 is now offset from and parallel to the second major surface 303 of the linkage portion 109. The first portion 111 of the patient support 103 extends in a horizontal direction perpendicular to the second major surface 303 of the linkage portion 109.

FIG. 4 shows another configuration in which the linkage portion 109 has been pivoted 180° from the configuration of FIG. 1 such that the first major surface 301 of the linkage portion 109 now lies horizontal against the support surface 102 (e.g., the floor) and the second major surface 303 of the linkage portion 109 faces vertically upwards. In this configuration, the patient support 103 has been pivoted 270° relative to the configuration of FIG. 1, such that the second portion 113 of the patient support 103 extends vertically upward from and perpendicular to the second major surface 303 of the linkage portion 109, and the first portion 111 of the patient support 103 extends in a horizontal direction over and parallel to the second major surface 303 of the linkage portion 109.

An advantage of the configuration of FIG. 4 is that it may facilitate easy loading and unloading of a patient to and from the patient support 103. In many cases, it can be challenging for a patient to get onto or be placed onto a conventional table for an imaging device. Often, particularly in the case of sick or infirm patients, this may require lifting patient from a gurney up onto a dedicated radiology table, which can be problematic for the medical staff. A table system 100 according to various embodiments may be lowered such as shown in FIG. 4 so that the bed 107 on which the patient is supported may be at a comfortable height for loading and unloading of the patient. For example, the bed 107 may be at a height of no more than about 50 cm, such as between 30 and 40 cm from the floor. This may allow a patient to easily climb onto or be lowered down onto the bed 107, which may be easier for both the patient and the medical staff members.

The patient support 103 may then be raised from the lowered position of FIG. 4 to a height suitable for an imaging scan (e.g., such that the patient support 103 may be positioned within the bore of an imaging device). In embodiments, the patient support 103 may be raised to raise the bed 107 to a height of one meter or more from the floor. FIG. 3 shows the patient support 103 raised to a maximum height for performing a scan of a patient supported in a horizontal lying position on the bed 107. The patient support 103 may be raised to any height between the lowered position in FIG. 4 and the raised position of FIG. 3 by controlling the relative pivoting motions of the base portion 101, linkage portion 109 and patient support 103. A control system 500 of the table system 100 (see FIG. 6) may coordinate the pivoting motions so that bed 107 stays generally horizontal as the patient support 103 is raised and lowered. The bed 107 may also be moved to an inclined position at any arbitrary angle (e.g., ±30° from the horizontal position shown in FIGS. 3 and 4). In embodiments, this may enable the patient to be supported in Trendelenburg and/or reverse Trendelenburg positions.

FIG. 5 illustrates the table system 100 in a configuration suitable for imaging a patient in a standing or weight-bearing position. In embodiments, the patient support 103 may be pivoted upwards by a pre-determined angle (e.g., 90°) from the lowered position shown in FIG. 4 to the position shown in FIG. 5. In the configuration of FIG. 5, the patient support 103 is supported in a cantilevered manner from the linkage portion 109 by the bracket members 119. The patient may be supported in a standing position on the platform 105, which is parallel to the support surface 102 (e.g., floor). The patient support 103 may be pivoted to any arbitrary angle with respect to the linkage portion 109, such as an angle between 0-90° from the surface 303 of the linkage portion 109 so that the weight of the patient may be partially supported by the platform 105 and partially supported by the bed 107. An imaging gantry of an imaging device (e.g., x-ray CT scanner) may scan the entire length of the patient without interference from either the linkage portion 109 or the base portion 101 of the table system 100.

Various examples of diagnostic imaging applications that may be performed on a human or animal patient in a weight-bearing position using the present table system 100 include, without limitation:

Imaging the bones of a foot. The three-dimensional relationships of the bones in the foot in a flatfoot deformity are difficult to assess with standard radiographs. CT scans demonstrate these relationships but are typically made in a non-weightbearing mode. The use of a weightbearing CT or other imaging apparatus may be useful in imaging the feet in patients with severe flexible pesplanus deformities and to better define the anatomical changes that occur.

Imaging of a limb (e.g. leg). Weight-bearing (CT) bilateral long leg hip to ankle examination and non-weight bearing cross-sectional imaging (CT) of the affected limb may be performed on the hip, knee and ankle, for example, and may be useful for determining variations in angulation and alignment accuracy for diagnosis and/or surgical planning.

Imaging of a spine. Weight bearing scanning (e.g., CT scanning) may be useful for improvements in the accurate diagnosis of degenerative spinal disorders by scanning a patient in the "real life" standing position. By scanning in the standing position, the spinal disc and facet joint compresses, which may enable more specific and precise diagnosis of degenerative spine disorders.

Imaging of a joint (e.g., knee). Weight bearing scanning (e.g., CT scanning) of the knee may enable more specific and precise diagnosis of the patella-femoral kinematics and may also be useful in surgical planning.

Angiography. Weight bearing angiography (e.g., CT angiography) may enable more accurate diagnosis, and may be used, for example, to examine the pulmonary arteries in the lungs to rule out pulmonary embolism, a serious but treatable condition. Weight bearing angiography may also be used to visualize blood flow in the renal arteries (those supplying the kidneys) in patients with high blood pressure and those suspected of having kidney disorders. Narrowing (stenosis) of a renal artery is a cause of high blood pressure (hypertension) in some patients and can be corrected. A special computerized method of viewing the images makes renal CT angiography a very accurate examination. This is also done in prospective kidney donors. Weight bearing angiography may also be used to identify aneurysms in the aorta or in other major blood vessels. Aneurysms are diseased areas of a weakened blood vessel wall that bulges out—like a bulge in a tire. Aneurysms are life-threatening because they can rupture. Weight bearing angiography may also be used to identify dissection in the aorta or its major branches. Dissection means that the layers of the artery wall peel away from each other—like the layers of an onion. Dissection can cause pain and can be life-threatening. Weight bearing angiography may also be used to identify a small aneurysm or arteriovenous malformation inside the brain that can be life-threatening. Weight bearing angiography may also be used to detect atherosclerotic disease that has narrowed the arteries to the legs.

A table system 100 such as shown and described may also be used to support a patient for interventional radiology procedures and external beam radiation (e.g., LINAC) treatment procedures.

The foregoing method descriptions are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not necessarily intended to limit the order of the steps; these words may be used to guide the reader through the description of the methods. Further, any reference to claim elements in the singular, for example, using the articles "a," "an" or "the" is not to be construed as limiting the element to the singular.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

What is claimed is:

1. A table system for use with an imaging device, comprising:
   a base portion that supports the table system over a support surface;
   a patient support comprising a platform sized and shaped to support a patient in a standing position and a bed sized and shaped to support the patient in a lying position, wherein the patient support is composed of at least one radiolucent material over a first portion of the patient support that includes at least the platform and the bed, and at least one reinforcing element composed of a non-radiolucent material located in a second portion at one end of the patient support adjacent to the platform to enable a patient supported on at least one of the platform and the bed to be imaged using an x-ray computed tomography (CT) imaging device over a full length of the patient passing through a bore of the x-ray computed tomography (CT) imaging device without imaging the at least one reinforcing element;
   a linkage portion coupled to the base portion and to the at least one reinforcing element of the patient support such that the linkage portion is pivotable with respect to both the base portion and the patient support; and
   a drive mechanism that drives the pivoting of the patient support with respect to the linkage portion and with respect to the base portion, the drive mechanism being configured to move the patient support between:
      a vertical position in which the platform is substantially parallel to the support surface,
      a horizontal position in which the bed is substantially parallel to the support surface; and
      one or more intermediate positions between the vertical position and the horizontal position;
   a first rotary shaft coupled between the linkage portion and the patient support; and
   a second rotary shaft coupled between the linkage portion and the base portion;
   wherein the drive mechanism includes a first motor disposed in rotational communication with the first rotary shaft to facilitate pivoting movement of the patient support relative to the linkage portion, and a second motor disposed in rotational communication with the second rotary shaft to facilitate pivoting movement of the linkage portion relative to the base portion.

2. The table system of claim 1, wherein the patient support is movable to any arbitrary angle between the vertical position and the horizontal position.

3. The table system of claim 1, wherein the linkage portion pivots with respect to the base portion, the patient support moves to lower the patient support to a first height above the support surface and raise the patient support to a second height above the support surface.

4. The table system of claim 3, wherein the bed is no more than about 50 cm above the support surface when the patient support is at the first height.

5. The table system of claim 3, wherein the bed is at least one meter above the support surface when the patient support is at the first height.

6. The table system of claim 3, wherein the patient support may be moved to any arbitrary height between the first height and the second height while maintaining the patient support in a horizontal position.

7. The table system of claim 3, wherein the drive mechanism drives the pivoting of the patient support with respect to the linkage portion to move the patient support from a horizontal position at the first height to a vertical position for performing a weight-bearing imaging scan.

8. The table system of claim 1, wherein the at least one radiolucent material comprises carbon fiber.

9. The table system of claim 1, wherein the patient support comprises a concave surface defining the bed.

10. The table system of claim 9, wherein the patient support comprises rounded surfaces to minimize x-ray attenuation by the patient support.

11. The table system of claim 1, wherein the patient support comprises a first pair of bracket members extending at least partially over first and second sidewalls of the linkage portion and coupled to the linkage portion via the first rotary shaft to enable the patient support to pivot with respect to the linkage portion, and the base portion comprises a second pair of bracket members mounted to the support surface and extending at least partially over the first and second sidewalls of the linkage portion, the second pair of bracket members coupled to the linkage portion via the second rotary shaft to enable the linkage portion to pivot with respect to the base portion.

12. The table system of claim 11, wherein the first and second pairs of bracket members have complementary angled surfaces.

13. The table system of claim 11, wherein the linkage portion comprises a support frame that supports rotary bearings enabling the first and second rotary shafts to rotate relative to the linkage portion.

14. The table system of claim 11, wherein the drive mechanism has a mirrored configuration that is rotated by 180° within an interior housing of the linkage portion.

15. The table system of claim 11, wherein the linkage portion comprises first and second major surfaces opposite to one another with the first and second sidewalls extending between the first and second major surfaces, and the linkage portion is pivotable at least 180° with respect to the base portion from a first position in which the first major surface of the linkage portion is oriented parallel to and facing away from the support surface and a second position in which the first major surface of the linkage portion is oriented parallel to and facing towards the support surface.

16. The table system of claim 15, wherein the patient support is pivotable at least 270° with respect to the linkage portion from a first position in which the platform is located at least partially over and parallel to the first major surface of the linkage portion and a second position in which the platform is located at least partially over and perpendicular to the second major surface of the linkage portion.

17. The table system of claim 15, wherein the linkage portion comprises third and fourth sidewalls extending between the first and second major surfaces on opposite sides of the linkage portion, the third and fourth sidewalls having a rounded contour to enable the linkage portion to pivot with respect to the support surface and the patient support with minimal clearance.

18. The table system of claim 1, wherein the base portion is coupled to at least one of a rotary bearing that enables the table system to be rotated on the support surface and a rail system that enables the table system to be translated along at least one direction on the support surface.

19. The table system of claim 1, wherein the drive mechanism comprises a first flexible drive element engaged with the first motor and the first rotary shaft, and a second flexible drive element engaged with the second motor and the second rotary shaft.

20. The table system of claim 19, wherein the first flexible drive element is further defined as a first drive chain, and wherein the second flexible drive element is further defined as a second drive chain.

\* \* \* \* \*